United States Patent [19]

Green

[11] Patent Number: 4,589,416

[45] Date of Patent: May 20, 1986

[54] SURGICAL FASTENER RETAINER MEMBER ASSEMBLY

[75] Inventor: David T. Green, Norwalk, Conn.

[73] Assignee: United States Surgical Corporation, Norwalk, Conn.

[21] Appl. No.: 722,198

[22] Filed: Apr. 11, 1985

Related U.S. Application Data

[63] Continuation of Ser. No. 538,988, Oct. 4, 1983, abandoned.

[51] Int. Cl.⁴ ............................................. A61B 17/04
[52] U.S. Cl. ......................... 128/334 C; 227/DIG. 1
[58] Field of Search .............. 128/325, 334 R, 334 C, 128/346; 227/DIG. 1 A–DIG. 1 C, 19, 15; 441/469, 476

[56] References Cited

U.S. PATENT DOCUMENTS

| | | |
|---|---|---|
| 1,287,583 | 12/1918 | Greenfield . |
| 1,654,371 | 12/1927 | Goodstein . |
| 1,868,100 | 7/1932 | Goodstein . |
| 3,086,208 | 4/1963 | Eby . |
| 3,166,072 | 1/1965 | Sullivan, Jr. |
| 3,258,012 | 6/1966 | Nakayama et al. . |
| 3,357,296 | 12/1967 | Lefever ............................ 128/334 C |
| 3,551,987 | 1/1971 | Wilkinson ........................ 128/334 R |
| 3,595,201 | 7/1971 | Oudenhoven . |
| 3,598,299 | 8/1971 | Johnson . |
| 3,606,888 | 9/1971 | Wilkinson ........................ 128/334 R |
| 3,641,804 | 2/1972 | Oudenhoven . |
| 3,744,495 | 7/1973 | Johnson . |
| 3,879,783 | 4/1975 | Giulie . |
| 3,899,914 | 8/1975 | Akiyama ........................... 128/334 R |
| 3,924,629 | 12/1975 | Akiyama . |
| 3,926,193 | 12/1975 | Hasson . |
| 4,026,294 | 5/1977 | Mattler ............................. 128/305 |
| 4,060,089 | 11/1977 | Noiles .............................. 128/334 C |
| 4,198,982 | 4/1980 | Fortner et al. .................... 128/334 C |
| 4,228,895 | 10/1980 | Larkin . |
| 4,246,903 | 1/1981 | Larkin . |
| 4,278,091 | 7/1981 | Borzone . |
| 4,304,743 | 12/1981 | Paradis ............................ 264/25 |
| 4,305,539 | 12/1981 | Korolkov et al. ................. 227/8 |
| 4,402,445 | 9/1983 | Green ............................... 227/19 |

FOREIGN PATENT DOCUMENTS 972731 10/1964 United Kingdom .

Primary Examiner—C. Fred Rosenbaum
Assistant Examiner—Gene B. Kartchner
Attorney, Agent, or Firm—John E. Nathan; Jeffrey H. Ingerman

[57] ABSTRACT

A unitary assembly of surgical fastener retainer members is disclosed. The assembly includes a plurality of retainer members, preferably of a resinous material, arranged in a surgically useful configuration and connected by flexible or frangible links preferably of the same material. The assembly facilitates handling of the retainer members and loading them into fastener applying apparatus.

20 Claims, 10 Drawing Figures

FIG.1
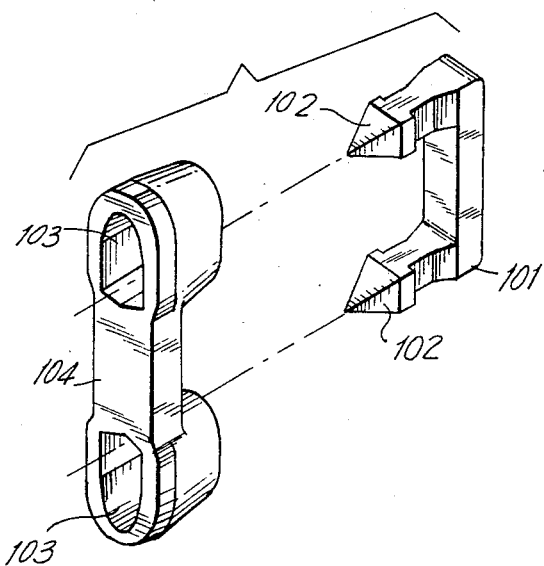
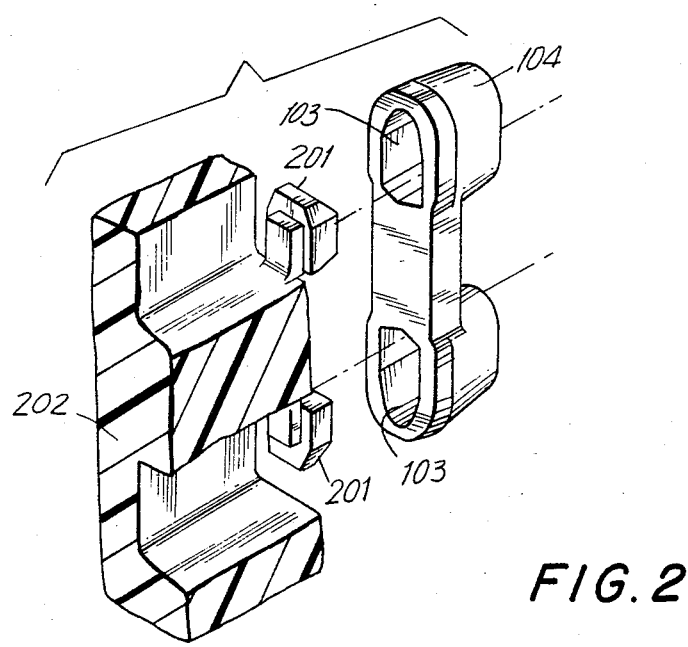
FIG.2

SURGICAL FASTENER RETAINER MEMBER ASSEMBLY

This is a continuation of application Ser. No. 538,988, filed Oct. 4, 1983, now abandoned, entitled SURGICAL FASTENER RETAINER MEMBER ASSEMBLY.

BACKGROUND OF THE INVENTION

This invention relates to surgical fasteners, and more particularly to a retainer member assembly for facilitating application of such surgical fasteners to body tissue.

Surgical stapling devices allow a surgeon to fasten body tissue by applying surgical staples. The staples may be applied singly in succession or a number may be applied simultaneously. Surgical staples are often made of metals such as tantalum or stainless steel, which are inert. Fasteners of magnesium, which fasteners are gradually absorbed by the body, are also known.

Non-metallic fasteners are also known and in some cases may have certain advantages over metal staples. For example, metal staples in the body may scatter X-rays and may therefore degrade the quality of radiographs.

However, metal staples also have certain advantages over non-metallic fasteners. They can be bent or crimped and will hold their new shape in or around tissue. In contrast, objects of non-metallic resinous materials are usually too resilient (i.e., elastic) to hold deformed shapes (assuming plastic flow does not occur). (As used herein, the term "resinous materials" means non-metallic materials, such as natural or synthetic polymers and resins, including protein-based materials, which are relatively flexible and elastic, and which may or may not be absorbable in the body.)

To circumvent this characteristic of resinous materials, surgical fasteners of these materials may be made in two parts: a fastener member and a retainer member. The prong or prongs of the fastener member are driven through one side of the tissue to be fastened and the retainer member interlocks with the prongs of the fastener member on the other side of the tissue to hold the entire fastener structure in place. One such fastener structure and apparatus for applying it are disclosed in Green U.S. Pat. No. 4,402,445 issued Sept. 6, 1983, which is hereby incorporated by reference in its entirety.

Such fastener structures are relatively small in size and typically are applied to tissue several at a time in rows. Because of their small size, loading the fastener and retainer members into the fastener-applying apparatus can be both tedious and time-consuming. The need exists for fastener structures that can be loaded quickly and easily.

SUMMARY OF THE INVENTION

In accordance with this invention, a unitary surgical fastener retainer member assembly is provided. The assembly comprises (1) a plurality of surgical fastener retainer members arranged in a configuration which has surgical utility (e.g., two parallel rows of members) and (2) yieldable (i.e., flexible or frangible) links, preferably of the same material as the retainer members, disposed between adjacent retainer members so that each retainer member is connected by at least one such link to at least one other retainer member in the array, all the retainer members thereby being connected directly or indirectly to each other. The present invention finds its greatest use with surgical fasteners of resinous materials, although the invention may be used with fasteners of other materials that have separate retainer members.

This assembly facilitates handling surgical fastener retainer members and greatly reduces the time and tedium involved in loading retainer members into fastener-applying apparatus; only a single loading of all the retainers at one time is required.

BRIEF DESCRIPTION OF THE DRAWINGS

The above and other advantages of the present invention will be more apparent after consideration of the accompanying drawings in which like parts are indicated by like reference characters throughout, and in which:

FIG. 1 is an exploded perspective view of an individual surgical fastener of the type with which the present invention is used;

FIG. 2 is a fragmentary exploded perspective view showing a typical latch means for retaining individual surgical fastener retainer members on a fastener-applying apparatus;

DETAILED DESCRIPTION OF THE INVENTION

A surgical fastener of the type with which the present invention can be used is shown in FIG. 1. The fastener includes fastener member 101, which has two prongs 102 that are driven through tissue to engage apertures 103 in retainer member 104. Both members may be made from a resinous material which may or may not be absorbable in the body. A preferred absorbable material is disclosed in copending, commonly-assigned Kaplan et al. U.S. patent application Ser. No. 436,056, filed Oct. 22, 1982, now U.S. Pat. No. 4,523,591, hereby incorporated by reference in its entirely.

Figure 3:
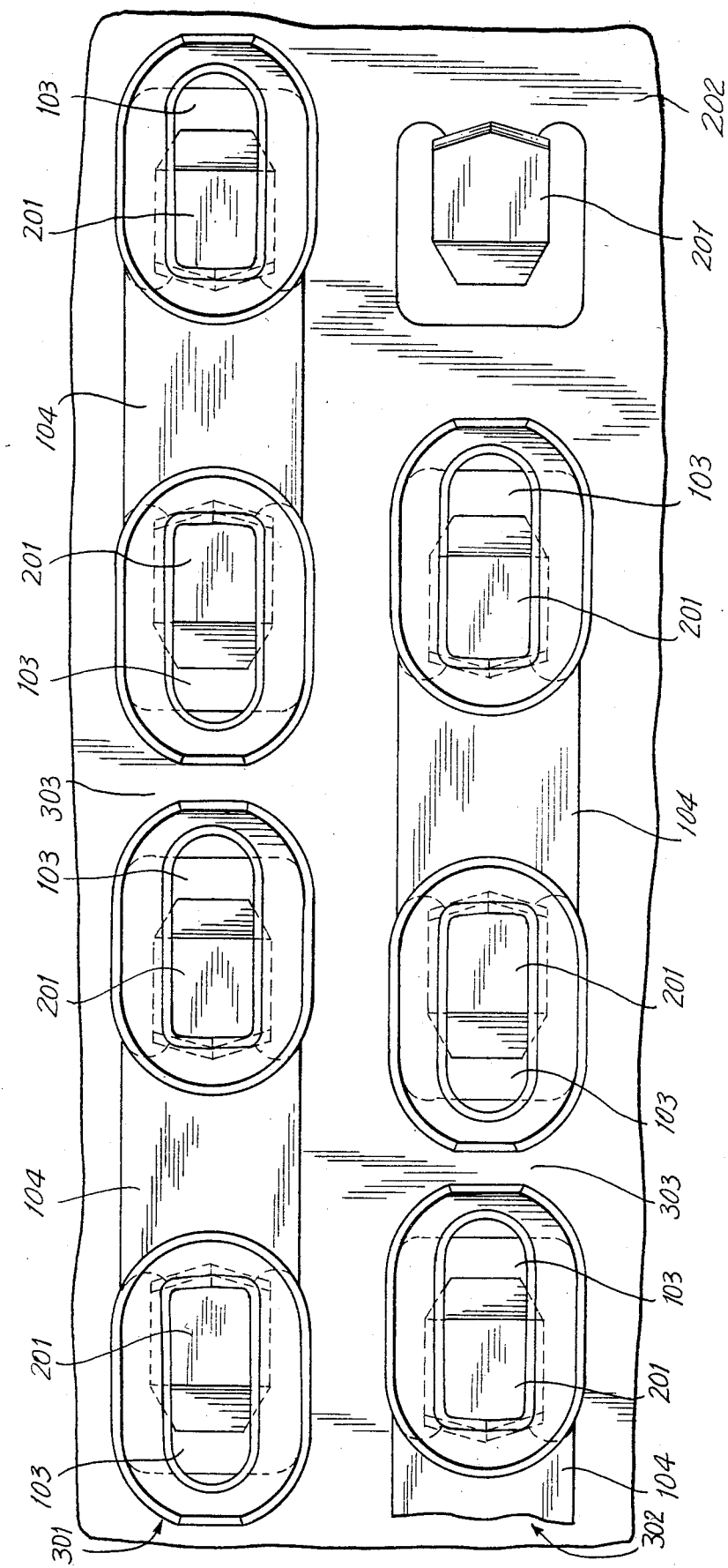
FIG. 3 is a fragmentary plan view of individual surgical fastener retainer members retained on the applying apparatus only by the latch means of FIG. 2.

These fasteners are applied either simultaneously or in succession in a surgically useful configuration to join tissue. One such configuration is shown in FIG. 3. This configuration is useful because it is linear and it provides good hemostasis. The latter is provided by the offset between rows 301 and 302 whereby the fasteners in one row clamp most tightly the tissue opposite gaps 303 in the other row.

The fasteners are applied using apparatus specifically designed for that purpose. As shown in FIGS. 2 and 3, for one such apparatus, lugs 201 engage apertures 103 to hold retainer member 104 securely to portion 202 of the body of the apparatus. Entry of prongs 102 into apertures 103 disengages lugs 201 at the moment at which lugs 201 are no longer needed to secure retainer members 104 to the apparatus. As explained above, each retainer member 104 must be individually loaded on lugs 201, in a tedious and time-consuming procedure.

Figure 4:
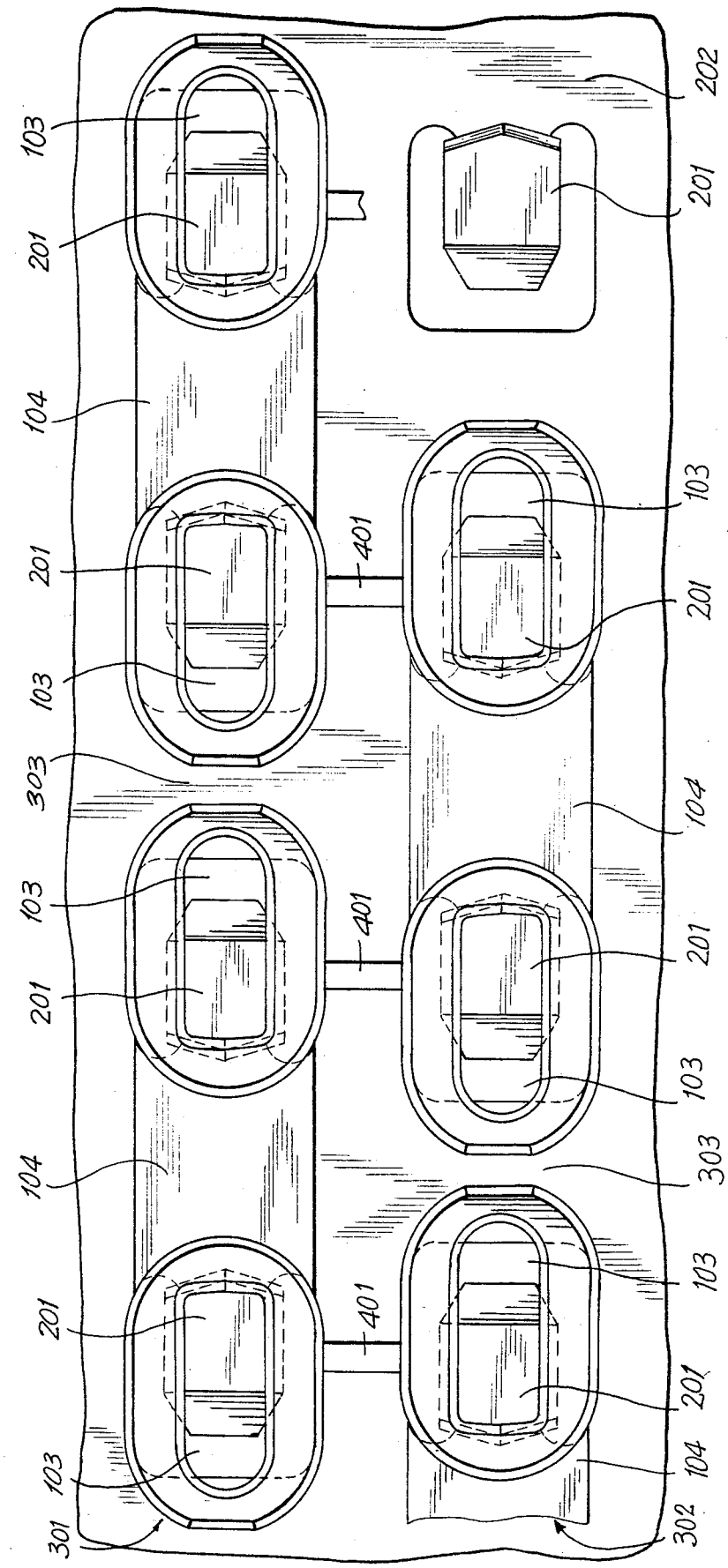
FIG. 4 is a fragmentary plan view of a surgical fastener retainer member assembly according to the present invention, which assembly is being retained on the applying apparatus.
Figure 5:
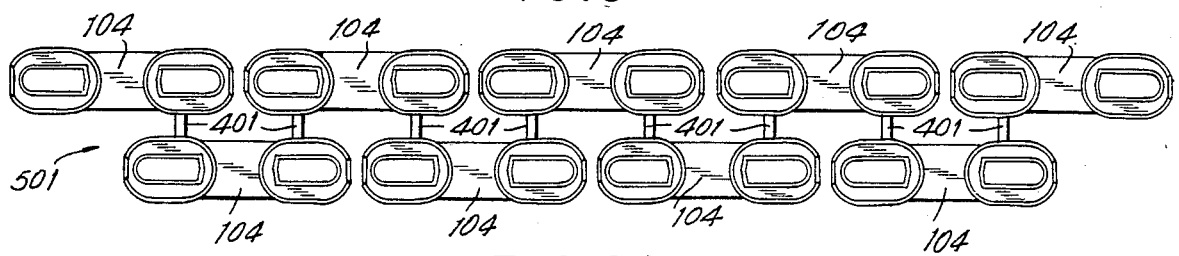
FIG. 5 is a plan view of the surgical fastener retainer member assembly of FIG. 4.
Figure 6A:
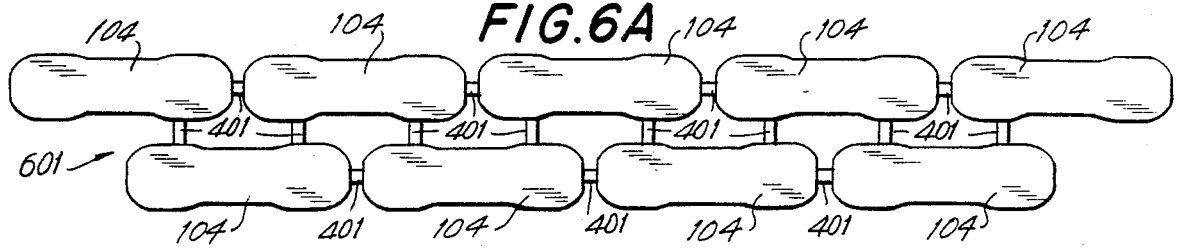
FIGS. 6A–6E are schematic plan views of five alternate configurations of surgical fastener retainer member assemblies according to the present invention.
Figure 6B:
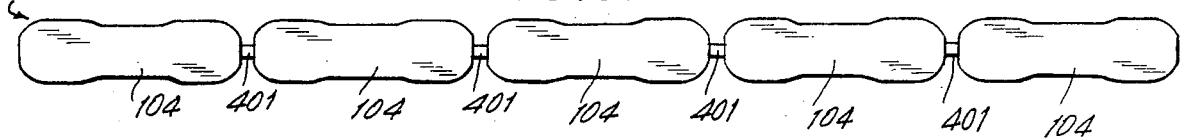
Figure 6C:
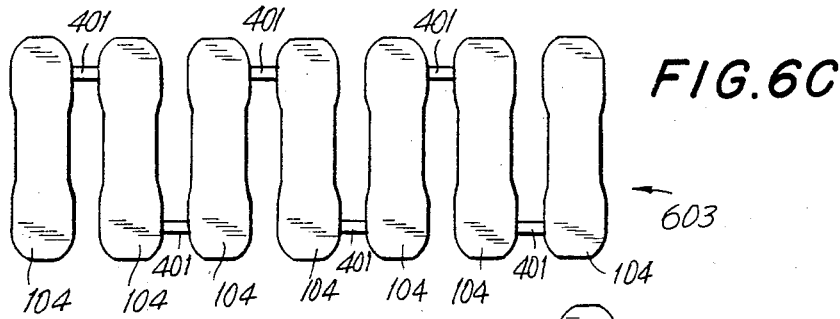
Figure 6D:
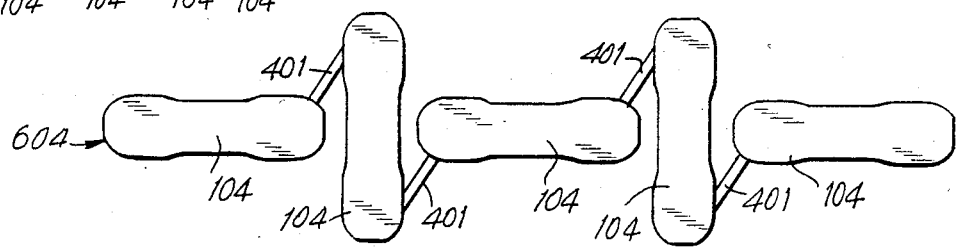
Figure 6E:
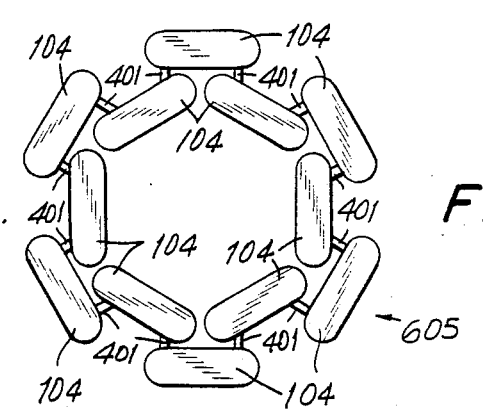

In accordance with the present invention, this procedure is expedited by the provision of a unitary assembly of retainer members. The retainer members are connected as shown in FIG. 4 by yieldable links 401, formed preferably of the same material as the retainer members. Retainer member assembly 501 of seven retainer members 104 is shown in FIG. 5. The number of retainer members in an assembly and the assembly configuration will vary depending on the particular surgical application. Other possible configurations 601, 602, 603, 604, and 605 are shown schematically in FIGS. 6A–6E. In particular, in configuration 601 of FIG. 6A, each retainer member is connected to adjacent retainer members by two links at each end thereof.

Yieldable links 401 must be capable of maintaining the integrity of assembly 501 during handling and loading but should be sufficiently flexible or frangible (i.e., breakable) so that once the fasteners are inserted into tissue, the links will yield sufficiently to flex with the fastened tissue. Specifically, when the surgical fasteners are applied the configuration of the fastener assembly will usually be planar. However, afterwards the fastened tissue may become non-planar. Links 401 should be sufficiently yieldable to allow the fastener array to follow the movement of the tissue. Accordingly, the links must either break or be flexible enough to allow relative motion among the fasteners.

Other benefits of the links are numerous. If a retainer member 104 is not properly latched into the applying apparatus 202, it still will be held in place by the neighboring retainer members 104 through the links 401. Similarly, if the surgeon inadvertently actuates the apparatus when not all of the fastener/retainer pairs are positioned to engage tissue, the mated fastener/retainer pairs that do not engage tissue will be connected to those mated fastener/retainer pairs that do engage tissue. The former remain associated with the fastened tissue and are therefore readily visible to the surgeon who can easily remove them by breaking the links with an instrument or by hand. Finally, the larger size of the assembly as compared to the size of the individual members makes the handling of the retainer members easier during the loading operation.

In summary, the surgical fastener retainer member assembly of this invention facilitates handling of surgical fastener retainer members and their loading into surgical fastener-applying instruments. The assembly of this invention provides for securing the retainer members in the instruments. One skilled in the art will recognize that the inventive principles disclosed herein can be practiced in other than the embodiments described, and the invention is not limited by those embodiments but only by the claims which follow.

I claim:

1. A unitary assembly of surgical fastener retainer members, for interengagement with a plurality of surgical fastener members for application to body tissue, said assembly comprising:
   a plurality of surgical fastener retainer members arranged in a surgically useful configuration, each of said retainer members having at least two spaced apertures; and
   one or more yieldable links disposed between the retainer members, each of said links having a cross-sectional area substantially less than the cross-sectional area of each retainer member intermediate the apertures in that retainer member, each of said retainer members being connected by at least one such link to at least one other retainer member so that all the retainer members are connected to each other for interengagement with said plurality of surgical fastener members as a unitary assembly.

2. The assembly of claim 1 wherein the yieldable link is flexible.

3. The assembly of claim 1 wherein the yieldable link is frangible.

4. The assembly of claim 1 wherein the configuration is linear.

5. The assembly of claim 4 wherein the yieldable link is flexible.

6. The assembly of claim 4 wherein the yieldable link is frangible.

7. The assembly of claim 4 wherein the linear configuration comprises a first row of retainer members and a second row of retainer members parallel and adjacent to the first row, the second row offset linearly with respect to the first row.

8. The assembly of claim 7 wherein the yieldable link is flexible.

9. The assembly of claim 7 wherein the yieldable link is frangible.

10. The assembly of claim 1 wherein the configuration is circular and comprises a first circle of retainer members and a second circle of retainer members concentric with the first circle, the second circle offset angularly with respect to the first circle.

11. The assembly of claim 10 wherein the yieldable link is flexible.

12. The assembly of claim 10 wherein the yieldable link is frangible.

13. The assembly of claim 1 wherein the retainer members are made of a resinous material.

14. The assembly of claim 13 wherein the resinous material is absorbable in the body.

15. The assembly of claim 1 wherein the link is made of the same material as the retainer members.

16. A surgical fastener retainer member assembly of a resinous material for use with a plurality of surgical fastener members for application to body tissue, comprising:
   a first row of surgical fastener retainer members of the resinous material;
   a second row of surgical fastener retainer members of the resinous material parallel and adjacent to the first row, the second row offset linearly with respect to the first row;
   each of said retainer members having at least two spaced apertures; and
   a plurality of yieldable links of the resinous material, each of said having a link cross-sectional area substantially less than the cross-sectional area of each retainer member intermediate the apertures in that retainer member, each of the retainer members in the second row connected by one of the links to each retainer member adjacent thereto in the first row for interengagement with said plurality of surgical fastener members as a unitary assembly.

17. The assembly of claim 16 wherein the yieldable links are flexible.

18. The assembly of claim 16 wherein the yieldable links are frangible.

19. The assembly of claim 16 wherein the linear offset is equal to one half the length of an individual retainer member with respect to the first row.

20. In combination;

apparatus for applying two-part surgical fasteners, each of the fasteners having a fastener member and a retainer member;

a plurality of fastener members positioned within the apparatus;

a corresponding number of retainer members positioned within the apparatus, each of said retainer members having at least two spaced apertures; and one or more yieldable links disposed between the retainer members, each of said links having a cross-sectional area substantially less than the cross-sectional area of each retainer member intermediate the apertures in that retainer member, each of the retainer members being connected by at least one such link to at least one other retainer member so that all the retainer members are connected to each other for interengagement with said plurality of fastener members as a unitary assembly when applied by said apparatus.

* * * * *